(12) United States Patent
Righi et al.

(10) Patent No.: US 6,673,044 B2
(45) Date of Patent: Jan. 6, 2004

(54) AUTOMATIC SAFETY SYRINGE

(76) Inventors: Nardino Righi, Via Cavour 7, 20047 Brugherio (Milano) (IT); Robèrto Rossi, Via Delle Ande 10, 20151 Milano (IT); Sergio Restelli, Via Quarto Peperino 333B, 00100 Roma (IT)

( * ) Notice: Subject to any disclaimer, the term of this patent is extended or adjusted under 35 U.S.C. 154(b) by 0 days.

(21) Appl. No.: 10/236,954

(22) Filed: Sep. 9, 2002

(65) Prior Publication Data
US 2003/0050601 A1 Mar. 13, 2003

(30) Foreign Application Priority Data
Sep. 10, 2001 (EP) .............................................. 01830575

(51) Int. Cl.⁷ ................................................ A61M 5/00
(52) U.S. Cl. ...................................................... 604/110
(58) Field of Search ................................ 604/110, 181, 604/187, 198, 218, 239–243, 263

(56) References Cited

U.S. PATENT DOCUMENTS

| | | |
|---|---|---|
| 4,994,034 A | 2/1991 | Botich et al. |
| 5,378,240 A | 1/1995 | Curie et al. |
| 5,843,034 A | 12/1998 | Redfern et al. |

FOREIGN PATENT DOCUMENTS

| | | |
|---|---|---|
| WO | 01/37902 A2 | 5/2001 |
| WO | 01/37908 A1 | 5/2001 |

*Primary Examiner*—David O. Reip
(74) *Attorney, Agent, or Firm*—Nixon & Vanderhye, P.C.; Frank P. Presta

(57) ABSTRACT

A disposable syringe (100) comprises an internally hollow syringe body (1) open at the front and rear, a plunger (40) slidable inside the syringe body (1) and provided at the rear with a shaft (50) operated manually through the rear end (80) thereof, an injection needle (10) integral with a needle carrier (11), a supporting body (20), accommodating the needle carrier (11) in a removable manner and engaging with the fore end (2) of the syringe body (1), a spring (30) disposed under compression between the needle carrier (11) and the supporting body (20), a diaphragm (62) removably mounted in the shaft head (51) to cover a shaft inner chamber and an opening (60) in the shaft head (51) cooperating with tongues (13) in the needle carrier (11) to cause disengagement of the needle carrier from the supporting body (20), when the plunger (40) reaches an injection stroke end, so that the spring (30), expanding, retract the needle carrier (11) which abuts against the diaphragm (62) causing disengagement or rupture thereof to allow the needle carrier (11) to enter the shaft body chamber, bringing the needle (10) into a safety position.

12 Claims, 4 Drawing Sheets

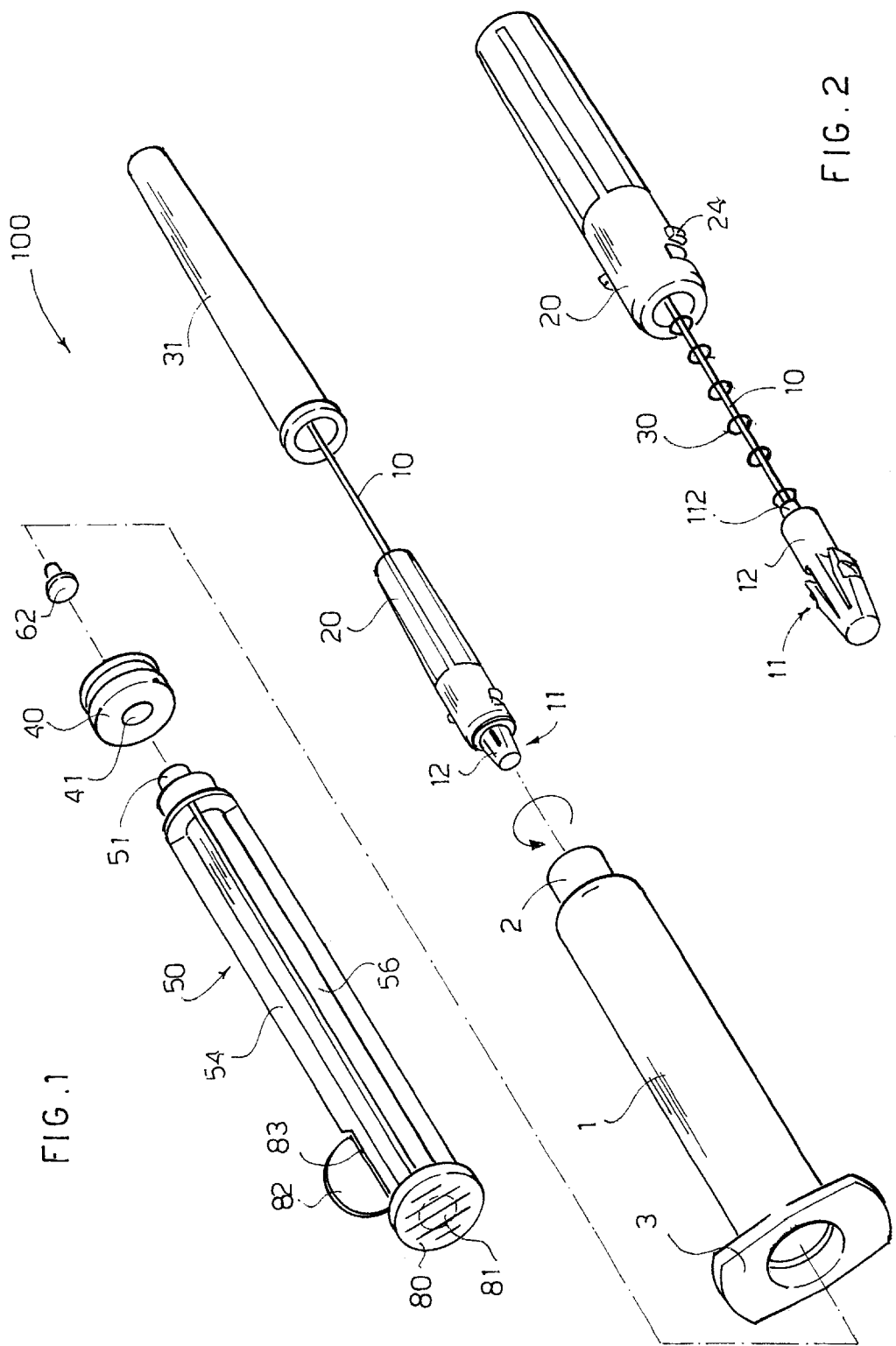

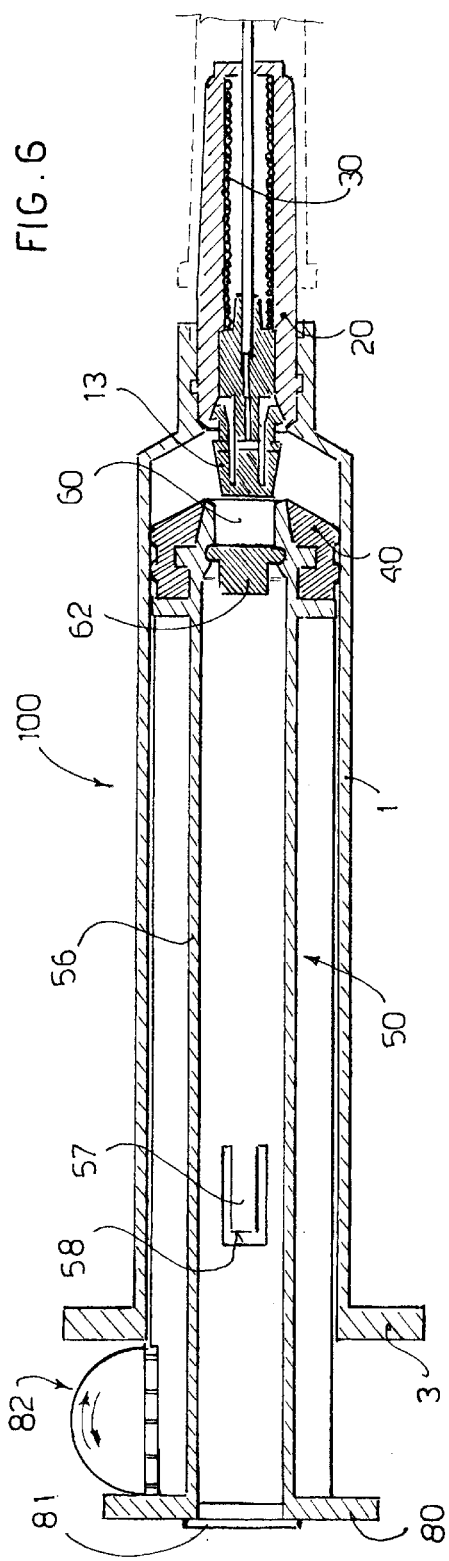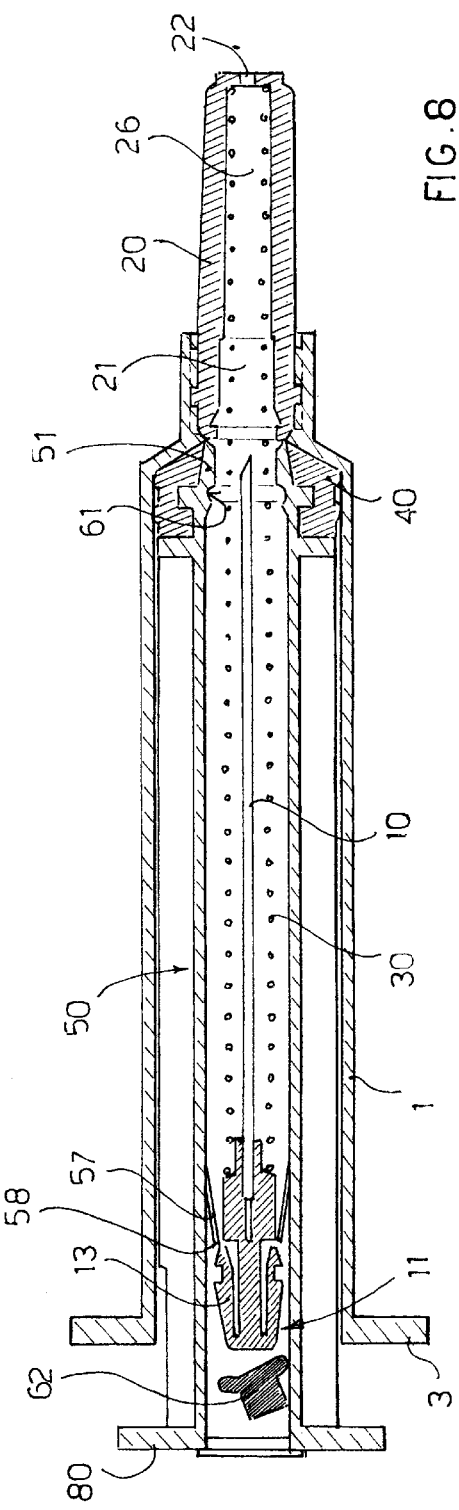

AUTOMATIC SAFETY SYRINGE

The present invention refers to an automatic safety syringe.

As is known, a syringe generally comprises a cylindrical body open at the rear to accommodate a plunger. An internally hollow needle is mounted at a head end of the syringe body. By retracting the plunger the liquid contained in a vial is drawn into the syringe body through the needle. By pressing on the plunger the liquid contained inside the syringe body is injected, through the needle, into the patient's body.

To comply with safety regulations and to avoid the transmission of infections diseases, syringes must generally be used just once and then discarded. For this reason there is a growing demand on the market for disposable syringes able to prevent further use thereof.

Moreover, syringes generally have drawbacks from a safety viewpoint. In fact, once the syringe has been used, the needle remains exposed at the head of the syringe body, with the risk of accidental injuries or needle sticks.

This drawback is overcome in part by European patent EP 0636381 which discloses a protective device for syringe needles. In this case, when the syringe plunger reaches the end of its stroke, the fore end of the plunger shaft catches the needle. When the injection is completed the user must manually retract the shaft; in this manner the needle is pulled by the head of the shaft inside the syringe body into a safety position which avoids accidental needle sticks.

Said solution has problems during hooking of the needle carrier and has the drawback that the user, having completed the injection, can forget to carry out retraction of the shaft, leaving the needle exposed and thus rendering the protective device ineffective.

Patent application PCT WO 99/37345 discloses a disposable safety syringe which provides a needle-covering sleeve axially mounted on the syringe body and slidable from a retracted position, in which it leaves the needle exposed to allow injection, to an advanced position in which it completely covers the needle, preventing re-use of the syringe and acting as a protection against accidental needle sticks.

Once the injection has been carried out the sleeve is automatically brought into the advanced safety position, by means of an automatic mechanism and without any intervention by the user. However, said solution presents a certain complexity for provision and movement of an additional element such as the needle-covering sleeve.

An object of the present invention is to eliminate the prior art drawbacks, providing an automatic safety syringe that is practical, versatile, cheap and simple to make.

Another object of the present invention is to provide such an automatic disposable safety syringe that is able to prevent further attempts at use.

Yet another object of the present invention is to provide such an automatic syringe that is extremely safe and able to prevent accidental injuries and tampering after it has been used.

These objects are achieved in accordance with the invention with the characteristics listed in appended independent claim 1.

Advantageous embodiments of the invention are apparent from the dependent claims.

The disposable syringe according to the invention comprises an internally hollow syringe body open at the front and rear, a plunger that can slide inside the syringe body with an injection stroke extending from a retracted syringe-filling position to a forward syringe-emptying position. The plunger is provided at the rear with a shaft or stem that can be operated manually and brought out of the syringe body through the rear end thereof. The syringe comprises an injection needle integral with a needle-carrier that can be engaged by means of a supporting body to the fore end of the syringe body.

The peculiarity of the invention is represented by the provision of an automatic system which intervenes automatically when the plunger reaches the end of the injection stroke. The automatic device is responsible for releasing the needle-carrier from the supporting body in order to push it inside a chamber defined in the shaft, so as to bring the needle integral with the needle carrier into a safety position.

Said automatic system comprises elastic means disposed under compression between the needle carrier and the supporting body, a diaphragm mounted in the head of the shaft to obstruct the inner chamber of the shaft, and engagement means provided in the head of the shaft able to cooperate with reciprocal engagement means provided in the needle carrier to cause disengagement of the needle carrier from the supporting body, when the plunger reaches the end of the injection stroke. In this manner the elastic means, on expanding, cause retraction of the needle carrier. The needle carrier thus abuts against the diaphragm causing disengagement or rupture thereof which allow the needle carrier to enter the shaft body chamber. In this manner the needle integral with the needle carrier is protected inside the chamber of the shaft body in a safety position.

The advantages of the disposable syringe according to the invention are evident. In fact, once the injection has been completed, the automatic system causes automatic, involuntary re-entry of the needle carrier inside the chamber defined inside the body of the shaft, thus placing the needle in a safety position which avoids accidental needle sticks.

Further characteristics of the invention will be made clearer by the detailed description that follows, referring to a purely exemplary and therefore non-limiting embodiment thereof, illustrated in the appended drawings, in which:

FIG. 1 is an exploded, axonometric view illustrating the automatic safety syringe according to the invention.

FIG. 2 is an axonometric exploded view of a needle carrier, a needle carrier support and a spring interposed therebetween;

FIG. 6 is a broken off axial sectional view, showing the syringe of FIG. 1 assembled and before use;

FIG. 8 is an axial sectional view, illustrating the syringe according to the invention after use, in which the shaft of the plunger is turned 90° with respect to FIG. 6.

Figure 5:
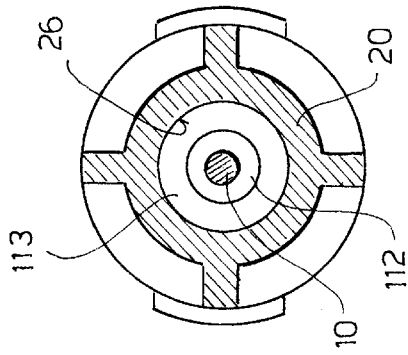
FIG. 5 is a cross sectional view along the plane of section V—V of FIG. 4.

The automatic safety syringe according to the invention, denoted as a whole by reference numeral 100, will be described with the aid of the figures.

With reference for now to FIG. 1 in particular, the syringe 100 comprises a cylindrical body 1, hollow on the inside, defining a cylindrical chamber. The body 1 has a flange 3 at the rear which protrudes radially outward.

The fore end of the body 1 is tapered and ends in an outwardly open head 2, in the form of a cylindrical tang, with a smaller diameter than the body 1. As shown better in FIG. 7, an inner thread 4 is formed in the inside surface of the head 2.

Figure 3:
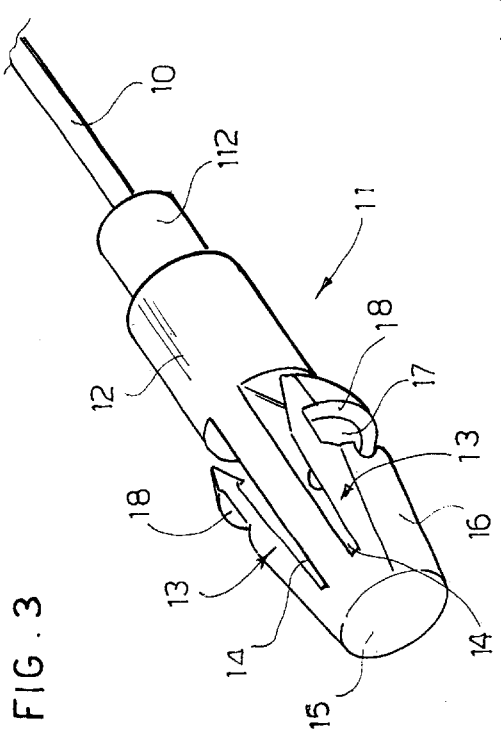
FIG. 3 is an enlarged, perspective view illustrating the needle carrier and the needle shown broken off.

A needle 10 is supported by a needle carrier 11. As better shown in FIGS. 2 and 3, the needle carrier 11 comprises a cylindrical block 12 ending at the front in a cylindrical tang 112 with a smaller diameter. In this manner a radial abutment surface 113 (FIG. 7) is defined between the tang 112 and the body 12 of the needle carrier 11. The tang 112 has an axial hole to receive one end of the needle 10.

The cylindrical block 12 has two flexible opposite facing tongues 13. The tongues 13 are obtained by means of respective longitudinal incisions 14 on the cylindrical body 12 of the needle carrier and are connected to the rear end 15 of the cylindrical body 12. Each tongue 13 has an outwardly tapered outer surface 16 ending in a slot or groove 17 which defines an abutment surface 18 that is radial with respect to the axis of the cylindrical body 12.

Figure 4:
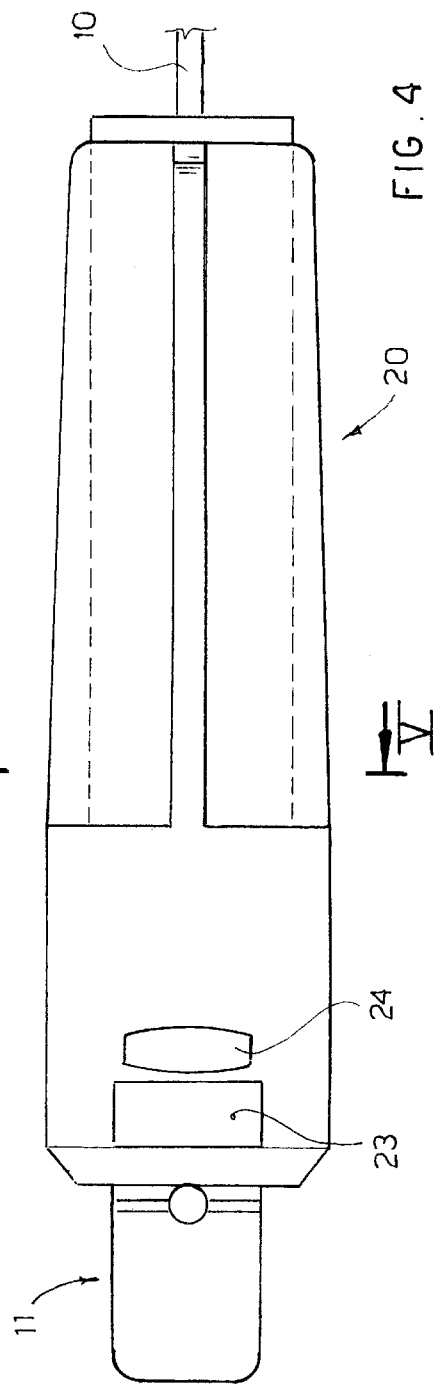
FIG. 4 is a side view of the needle carrier support with the needle carrier assembled therein.
Figure 7:
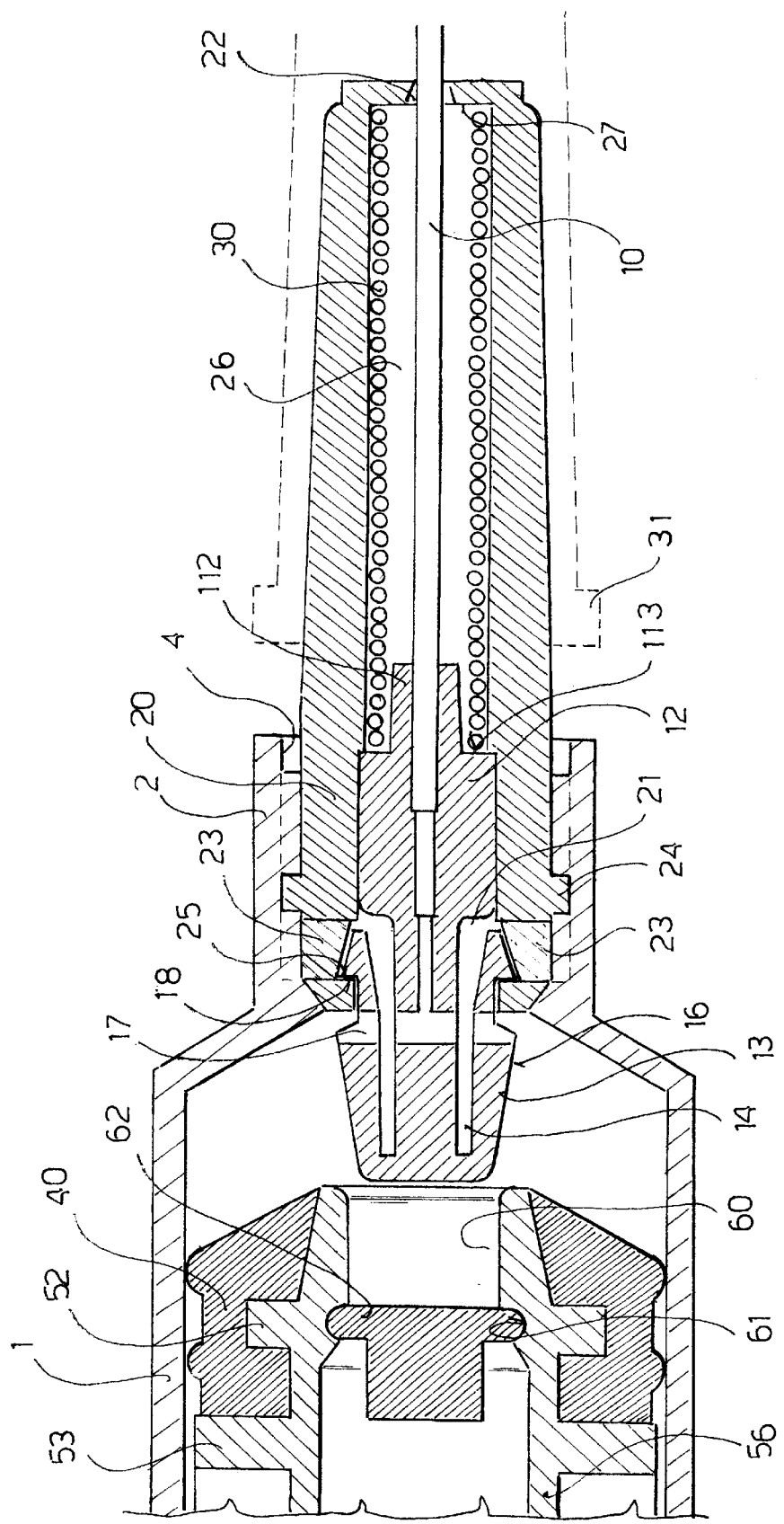
FIG. 7 is an enlarged view of a detail of FIG. 6.

The needle carrier 11 is inserted in a supporting body 20. With reference to FIGS. 4, 5 and 7, the supporting body 20 has a substantially cylindrical or frusto-conical shape. The supporting body 20 is hollow on the inside and has an axial cylindrical housing 21, able to receive the cylindrical body 12 of the needle carrier. Inside the supporting body 20 an axial chamber 26 is defined, communicating with an axial hole or channel 22, formed in the front end wall of the supporting body 20. The hole 22 is able to allow the passage of the needle 10 which protrudes axially from the supporting body 20. Around the hole 22 the front wall of the supporting body 20 defines an annular abutment surface 27 on the inside.

In the vicinity of the rear end of the supporting body 20 two radial slots 23 are provided, disposed in diametrically opposite positions, communicating with the housing 21 so as to define an edge part 25 in the rear end of the supporting body 20. Forward of the radial slots 23 two transverse tongues 24 are provided which protrude radially outward from the outer side surface of the supporting body 20. The tongues 24 are of such a thickness as to be able to engage in the thread 4 provided on the inside of the head 2 of the syringe body 1.

As shown in particular in FIG. 7, the needle carrier 11 is inserted inside the supporting body 20 and a spring 30 is interposed between the needle carrier 11 and the supporting body 20. The spring 30 is arranged under compression around the needle 10, inside the inner chamber 26 of the supporting body 20. One end of the spring 30 abuts against the abutment surface 113 of the body 12 of the needle carrier and the other end of the spring 30 abuts against the abutment surface 27 of the front part of the supporting body 20.

In particular the protruding front part of each tongue 13 of the needle carrier engages into the respective radial slot 23 of the supporting body 20, the edge 25 of the supporting body 20 engages into the two grooves 17 of the two tongues 13 and the abutment surface 18 of the tongues 13 abuts against the edge 25 of the supporting body 20. In this manner the needle carrier 11 is firmly retained and held in the axial position inside the supporting body 20, despite the fact that the spring 30 is compressed and tends to push the needle carrier away from the supporting body 20.

When the tongues 13 are pressed inward, the edge 25 of the supporting body 20 is released from the grooves 17 of the tongues 13 and the needle carrier 11 can be extracted from the supporting body 20. In this manner the needle carrier 11 is of the interchangeable type and can be replaced according to the type of needle 10 to be used.

The assembly formed by the needle carrier 11 and supporting body 20 is mounted in the head 2 of the syringe body by screwing. To be precise, the radial tongues 24 of the supporting body are screwed into the inner thread 4 of the head 2 of the syringe body. The needle 10 is covered by means of a needle cover or guard 31 (FIG. 1) which snaps or screws onto the supporting body 20.

A plunger 40 is made of plastic or rubber material and has such a shape as to be able to slide tightly inside the chamber of the syringe body 1. The plunger 40 has an axial through cavity 41 able to engageably receive a head 51 of a plunger shaft or stem 50.

The shaft 50 comprises a hollow cylindrical body 56 internally defining an axial chamber. Four longitudinal walls 54 depart radially from the lateral outside surface of the body 56 of the shaft. As shown in FIGS. 6 and 7, two flexible tongues 57 disposed longitudinally in diametrically opposite positions are provided in the inner wall of the cylindrical body, at the rear. Each tongue 57 has an inwardly tapered surface which ends at the rear with an abutment surface 58.

The shaft 50 ends at the rear with a circular flange 80 disposed transversally. The flange 80 is provided with a stopper 81 to close the axial chamber of the body 56 of the shaft 50. The rear flange 80 forms a resting surface for manual operation of the syringe shaft by the user.

A safety device 82 is disposed longitudinally at the rear end of a wall 54 of the shaft 50 in contact with the flange 80. The safety device 82 is in the form of a semicircular plate removably secured on the wall 54, by means of a tearable joint 83, so as to be able to be removed by the user. The safety device 82 protrudes outward, so as to be able to abut against the flange 3 of the syringe body to limit the injection stroke of the shaft 50.

As shown in FIG. 7, the head 51 of the shaft has a first annular flange 52 which engages in an annular seat of the plunger cavity 41 and a second annular abutment flange 53 against which the base of the plunger 40 abuts. The head 51 of the shaft 50 has at the front a cylindrical opening 60 open toward the outside. Inside the cylindrical opening 60 is an annular seat 61 (FIG. 8) recessed radially inward.

Within annular seat 61 of opening 60 of the shaft head is housed a diaphragm 62 serving to close the inner chamber of the shaft body to prevent liquid from entering the chamber. The diaphragm 62 is in the form of a circular plate with a side edge which substantially reproduces the profile of the annular seat 61. The diaphragm 62 is removably housed in the annular seat 61, but with a sufficiently tight seal to allow compression of the liquid during injection. The outside diameter of the diaphragm 62 is slightly less than the inside diameter of the body 56 of the shaft.

Operation of the syringe 100 according to the invention is described hereunder.

In an initial situation the needle-carrier 11 is mounted in the supporting body 20 with the edge 25 of the supporting body 20 engaged in the grooves 15 of the tongues 13 of the needle-carrier 11 and the spring 30 compressed between the supporting body 20 and the needle carrier 11. The supporting body 20 is mounted in the head 2 of the syringe body 1. In this situation, as shown in FIGS. 6 and 7, the inner duct of the needle 10 communicates with the inner chamber of the syringe body 1 through the axial channel of the body 12 of the needle carrier and the rear part of the grooves 17 of the tongues 13 of the needle carrier. The needle guard 31 is mounted on the supporting body 20 and keeps the needle 10 covered. The plunger 40 is mounted on the head of the shaft 50 and is situated inside the chamber of the syringe body 1. The diaphragm 62 is mounted inside the opening 60 in the head of the shaft 50. The safety device 82 is mounted on the wall of the shaft 50.

Initially, the needle guard 31 is removed, the needle 10 is placed in the liquid to be aspirated, and the user retracts the shaft 50 by means of the operating flange 80 of the shaft 50. The consequent retraction of the plunger 40 causes a vacuum in the chamber of the syringe body 1, thus the liquid is drawn into the chamber of the syringe body 1 through the needle 10. Obviously the syringe could alternatively be pre-filled. The safety device 82 which stops the injection stroke of the shaft 50 is subsequently removed.

When the injection is carried out, the user presses the rear part 80 of the shaft 50 causing a forward movement of the plunger 40 which pushes the liquid which is injected through the needle 10, passing through the grooves 17 and through the axial channel of the needle carrier 11.

When the plunger 40 arrives in the vicinity of the end point of its stroke, the tongues 13 of the needle carrier 11 enter the opening 60 in the head 51 of the shaft. Since the surfaces 16 of the tongues 13 are tapered, the tongues 13 bend inward and the abutment surface 18 of the tongues 13 disengages from the abutment surface 25 of the edge of the supporting body 20. As a result the spring 30, which was compressed, expands, pushing the needle carrier 11, which is released from the supporting body 20, axially rearward.

At the same time the rear surface 15 of the needle carrier abuts against the front surface of the diaphragm 62 causing disengagement of the diaphragm from its seat 61 inside the opening 60 of the head of the syringe shaft. As a result the needle carrier 11 is pushed by the spring 30 inside the chamber of the body 56 of the shaft 50 and the diaphragm 62 is also pushed by the needle carrier 11 inside the chamber of the body 56 of the shaft. In this manner the needle 10 which is integral with the needle carrier 11 is in a safety position inside the chamber of the shaft body.

It should be noted that the needle carrier 11, in its retraction stroke inside the body 56 of the shaft, encounters the tongues 57. Consequently the tapered surface 16 of the tongues 13 of the needle carrier slides on the tapered surface of the tongues 57 of the body 52 of the shaft. As a result both the tongues 13 of the needle carrier and the tongues 57 of the shaft bend inward until the fore end of the tongues 13 of the needle carrier pass the rear end of the tongues 57 of the shaft. In this situation, as shown in FIG. 8, the rear end of the tongues 13 of the needle carrier is in abutment against the fore end 58 of the tongues 57 of the shaft, preventing the needle carrier 11 from leaving the inner chamber of the shaft.

In the present description a diaphragm 62 able to be pushed by the needle carrier 11 inside the chamber of the body of the shaft is shown. However, the diaphragm 62 can be of the breakable type and therefore can be broken by the rear surface of the needle carrier to allow entry of the needle carrier into the shaft chamber.

Numerous changes and modifications of detail within the reach of a person skilled in the art can be made to the present embodiment of the invention, without thereby departing from the scope of the invention, set forth in the appended claims.

What is claimed is:

1. A disposable syringe (100) comprising:
   a syringe body (1) hollow on the inside and open at the front and rear,
   a plunger (40) slidable inside the syringe body (1) with an injection stroke extending from a retracted syringe-filling position to a forward syringe-emptying position, said plunger (40) being provided at the rear with a shaft (50) that can be operated manually and brought out of the syringe body through the rear end (80) thereof,
   an injection needle (10) integral with a needle carrier (11),
   a supporting body (20), able to receive the needle carrier (11) in a removable manner and engageable to the fore end (2) of the syringe body (1), characterized in that it comprises
   elastic means (30) disposed under compression between said needle carrier (11) and said supporting body (20),
   a diaphragm (62) mounted in the head (51) of said shaft (50) to close an inner chamber formed axially in the body (56) of said shaft, said diaphragm being mounted removably or being breakable, and
   engagement means (60) provided in the head (51) of said shaft to cooperate with reciprocal engagement means (13) provided in said needle carrier (11) to cause disengagement of said needle carrier from said supporting body, when the plunger (40) reaches the end of the injection stroke, so that said elastic means (30) are released, causing retraction of said needle carrier which abuts against said diaphragm (62) causing disengagement or rupture thereof to allow entry of said needle carrier (11) into the chamber of the shaft body and carrying the needle (10) in a safety position.

2. A syringe according to claim 1, characterized in that said reciprocal engagement means of said needle carrier (11) comprise flexible tongues (13) obtained by means of respective longitudinal notches (14) on the body of said needle carrier, each tongue (13) comprising a groove (17) defining an abutment surface (18) able to engage with an abutment surface (25) defined on the edge of said supporting body (20) to retain said needle carrier (11) inside said supporting body (20) against the action of said elastic means (30).

3. A syringe according to claim 2, characterized in that said tongues (13) comprise a tapered outside surface (16) and said engagement means of the shaft head comprise an opening (60) disposed at the fore end of the shaft head, so that when the tapered surface (16) of the tongues (13) engages with the edge of said opening (60), the tongues (13) bend inward causing the needle carrier to disengage from the supporting body.

4. A syringe according to claim 3, characterized in that inside said opening (60) in the shaft head is an annular seat (61) able to accommodate said diaphragm (62) in a removable manner.

5. A syringe according to claim 4, characterized in that said diaphragm (62) is in the form of a circular plate with a smaller diameter than the diameter of said chamber defined inside the body (56) of said shaft, so that said diaphragm (62) can be expelled into said chamber defined inside the cylindrical body of the shaft.

6. A syringe according to claim 1, characterized in that said needle carrier has at its fore end a cylindrical tang having a smaller diameter than that of the body of the needle carrier so as to define a radial abutment surface on which one end of said elastic means abuts.

7. A syringe according to claim 6, characterized in that said elastic means (30) are a helicoidal spring disposed inside said supporting body around said needle (1) with one end abutting on said abutment surface (113) of the needle carrier (11) and the other end abutting on an abutment surface (27) defined in the fore part of the supporting body, around a channel (22) which allows the needle (10) to protrude axially outward.

8. A syringe according to claim 1, characterized in that locking means able to lock said needle carrier in position when it is disposed inside the chamber of the body of the plunger shaft, after the injection has been carried out, are provided in the inner surface of said body of the plunger shaft.

9. A syringe according to claim 8, characterized in that said locking means are flexible longitudinal tongues (57) having a tapered surface able to cooperate with the tapered surface (16) of said tongues (13) of the needle carrier and having a rear abutment surface (58) able to abut with the forward surface of said tongues (13) of the needle carrier.

10. A syringe according to claim 1, characterized in that it comprises safety means able to prevent the plunger from reaching the injection stroke end position.

11. A syringe according to claim 10, characterized in that said safety means (82) comprise a plate that can be removed by the user, disposed on the outer surface of said shaft (50) to go into abutment against the rear edge of the syringe body (1), before the plunger (40) reaches the end of the injection stroke.

12. A syringe according to claim 1, characterized in that said supporting body comprises tongues protruding radially from the outer surface thereof to engage in a thread formed in the inner surface of the head of said syringe body.

\* \* \* \* \*